US012171945B2

(12) United States Patent
Liu (10) Patent No.: US 12,171,945 B2
(45) Date of Patent: Dec. 24, 2024

(54) NOSE RESPIRATOR DEVICE

(71) Applicant: Amy Zhang Liu, Apex, NC (US)

(72) Inventor: Amy Zhang Liu, Apex, NC (US)

( * ) Notice: Subject to any disclaimer, the term of this patent is extended or adjusted under 35 U.S.C. 154(b) by 626 days.

(21) Appl. No.: 16/868,538

(22) Filed: May 7, 2020

(65) Prior Publication Data

US 2021/0346632 A1    Nov. 11, 2021

(51) Int. Cl.
*A61M 16/06* (2006.01)
*A61M 16/20* (2006.01)
*A61M 25/02* (2006.01)

(52) U.S. Cl.
CPC ........ *A61M 16/0666* (2013.01); *A61M 16/20* (2013.01); *A61M 25/02* (2013.01); *A61M 2025/0226* (2013.01); *A61M 2205/0238* (2013.01); *A61M 2205/75* (2013.01)

(58) Field of Classification Search
CPC .......... A61M 2025/0226; A61M 16/06; A61M 16/204; A61M 16/205; A61M 16/0683; A61M 16/0666; A61M 16/20; A61M 16/206; A61M 16/107; A62B 23/06; A62B 9/02; A62B 18/025; A62B 7/10; A61B 9/02
See application file for complete search history.

(56) References Cited

U.S. PATENT DOCUMENTS

2009/0007919 A1*  1/2009  Dolezal ............... A62B 7/10
                                                128/206.11
2023/0072399 A1*  3/2023  Zhao ................. A61M 16/0672

FOREIGN PATENT DOCUMENTS

FR          684622    *  6/1930
KR        102044469   * 11/2019

* cited by examiner

*Primary Examiner* — Michael J Tsai
*Assistant Examiner* — Rachel T. Smith
(74) *Attorney, Agent, or Firm* — MagStone Law, LLP; Enshan Hong (57) ABSTRACT

A nose respirator device with a holder connected to a base. The holder has a top which is configured to sit on a nasal bridge and is joined on each side with an arm which extends downward and each arm joins the base which is configured to sit across a subnasale underneath nose tip. The base contains two separate open cavities, each open cavity has an upper opening shaped like a cone suitable for insertion into a nostril. Each open cavity of the two separate open cavities can be further divided by a separator into two channels. Valves installed along inside wall of each channel control air flow as the valves are configured to open only in one direction when being pushed by air current. Filters can be fitted into each cavity or each channel within each cavity for air cleaning.

7 Claims, 7 Drawing Sheets

NOSE RESPIRATOR DEVICE

BACKGROUND OF THE INVENTION

1. Field of the Invention

The present invention relates to a nose respirator device, more particularly to a nose respirator device that can be easily worn and can contain changeable filters to filter air. The present invention also relates to a nose respirator device, specifically a nose respirator device that allows inhaled air and exhaled air to pass through separate channels. The present invention further relates to a nose respirator device, more uniquely a nose respirator device that contains valves for ensuring one-way air flow through respective channels according to desired directions.

2. Description of Related Art

Human beings need to protect their respiratory system from inhaling harmful or undesirable substances, which include pathogens, allergens, and pollutants. Very often, they wear facial masks or facial respirators to achieve this protection. Less commonly, they wear nose filters, nose masks or nose respirators for the same purpose. Although facial masks or respirators are effective in achieving certain protection against respiratory damage, they have the following drawbacks:

1. They cover both the nose and the mouth at the same time and thus prevent independent function of each. For example, a person cannot eat, drink, or smoke while wearing a facial mask or facial respirator. Expressing language for deaf audience through lip-reading is also hindered by the mouth covering.

2. They cover a large area of facial surface and hinder skin ventilation. Wearing them for a long time is uncomfortable, especially in the summer or in a high temperature environment. They can cause skin irritations or even rashes. Some people also cannot wear facial masks or facial respirators due to their skin sensitivity to them or claustrophobia caused by them or out of religious beliefs.

3. They often lead to fogging on glasses or goggles and thus create visual problems.

4. They interfere with many activities, such as oral communications, facial recognition, showering, hair-cutting, dental work, and oxygen therapy.

5. They are not convenient to be worn together with other things, such as a helmet, and can easily get wet in a rainy environment or in taking a shower.

6. They are not handy for carrying around and storing.

7. They use a larger amount of materials than nose filters or nose masks or respirators do.

8. The cost of masks, especially high-end respirators, is not cheap.

9. They create a large amount of waste when disposed of after use.

10. They are often made as non-reusable.

An alternative way of preventing entry of harmful or undesired substances into the respiratory system is to use nose filters or nose masks or respirators. Currently there are several types of nose respirators. Collectively, they have the following drawbacks:

1. Inhaled and exhaled air pass through the same channel and use the same filter. This will present a problem in some situations, such as retained pathogens in the filter that are released by the patient wearing the device can re-enter the patient's respiratory system with inhalation.

2. Filters are inserted deep into nostrils, which creates an uncomfortable feeling to users.

3. Filters are limited in size by the natural volumes of nostrils. Filters are not convenient for amendment with other features.

4. Interfering with the oxygen therapy where oxygen-feeding tubes need to be inserted into nostrils.

SUMMARY OF THE INVENTION

The primary objective of the present invention is to provide a nose respirator device that consists of a holder and a base. The holder sits on the nasal bridge to secure the device onto the nose. The base contains multiple cavities for retaining filters. When the nose respirator device has filters-inserted into the cavities and is worn by a user, particles suspended in the air can be prevented from being inhaled into the respiratory system.

The secondary objective of the present invention is to provide separate channels for breathing air into and out of the nose. This divided air flow makes breathing easier than a common filter does. It also reduces the retention of potential pathogens within the respiratory system and extends the duration of the filter's usability.

The third objective of the present invention is to provide "valves" inside each channel for desired "one-direction" air flow in each channel and for preventing "back flow" of air current.

The fourth objective of the present invention is to provide mechanisms for attaching other devices onto the basic devices of the present invention.

The fifth objective of the present invention is to provide mechanisms for creating multiple stylistic designs that fit on the basic devices of the present invention.

Other objectives, advantages and novel features of the invention will become more apparent from the following description when taken in conjunction with the accompanying drawings.

BRIEF DESCRIPTION OF THE DRAWINGS

FIG. IA is a perspective view of a first embodiment of a basic structure for the nose respirator device in accordance with the present invention in which all open-ended cavities within the base of the device are shown with dashed lines;

FIG. IB is a side plan view of the nose respirator device in FIG. IA;

FIG. IC is a bottom plan view of the nose respirator device in FIG. IA;

FIG. 3 is a third embodiment of a nose respirator in accordance with the present invention in which the air flowing into and out of the channels are controlled by multiple "valves" (shown in FIG. 3A as a bottom plan view and in FIG. 3B as a perspective view), placed in positions arranged for preventing "back flow";

FIG. 4 is a fourth embodiment of a nose respirator device in accordance with the present invention in which an additional attachment (shown in FIGS. 4A and 4B for side view and bottom view, respectively) is fixed onto the bottom of the base of the device for holding extra things, such as a piece of membrane;

FIG. 5 is a fifth embodiment of a nose respirator device in accordance with the present invention in which an additional attachment (shown in FIGS. 5A and 5B for perspective and bottom views, respectively) is fixed onto the outside of the exhaling channels that point to the side of the device's base;

DETAILED DESCRIPTION OF THE PREFERRED EMBODIMENT

The nose respirator in accordance with the present invention has a holder (10) and a base (20). The holder is to be appreciated for its primary function of hanging the device onto the nasal bridge (A) and for connecting to the device's base (20), which is placed across the subnasale (B) under the nose tip (C). The base is to be appreciated for its basic function of containing multiple open-ended cavities (30) used for retaining filters (not shown) that can filter air flowing through the cavities. The connection between the holder and the base can be achieved through different mechanisms including one selected from the group consisting of melding together, joining together, adhering together, hinging together, coupling together, etc.

Figure 1A:
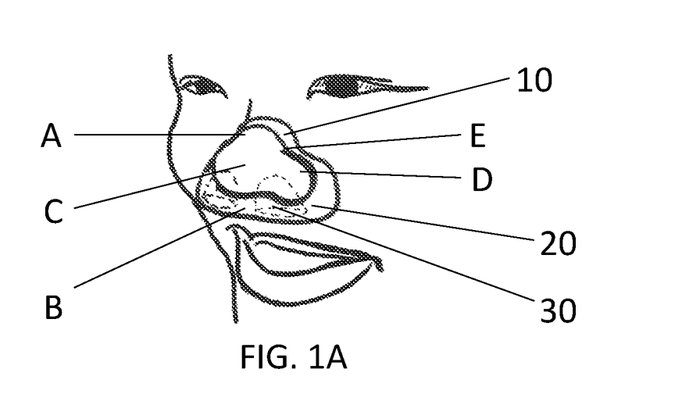
Figure 1B:
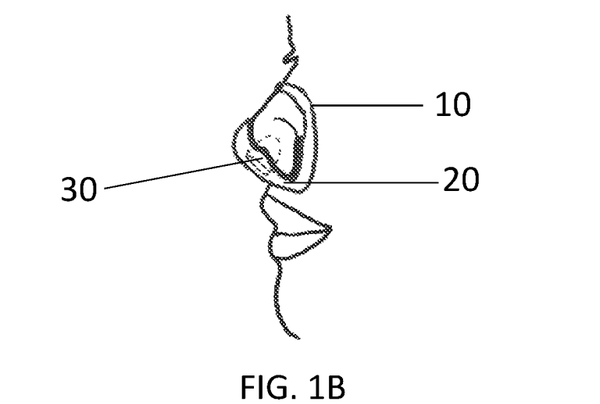
Figure 1C:
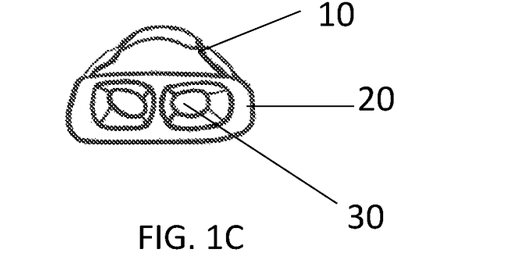

With reference to the series of FIGS. IA to IC, a first embodiment of a nose respirator device in accordance with the present invention is shown and has the holder (10) and the base (20). The holder in the first embodiment is shaped as a triangle with its top molded for comfortably sitting on and securely hanging from the nasal bridge (A) and its two side arms made to extend down the outside of each of the nose's alae (D) to join with the base (20). The two side arms have a mechanism of pinching inward towards the nasal ridge on the recessed areas (E) above the alae for further securing the holder on the nose. The base sits across the subnasale (B) under the nose tip (C) and has multiple cavities (30) that open on both ends, each shaped like a cone in the upper extruded part for inserting into the nostril. A filter (not shown) is inserted into each cavity from the bottom of the cavity.

Figure 2A:
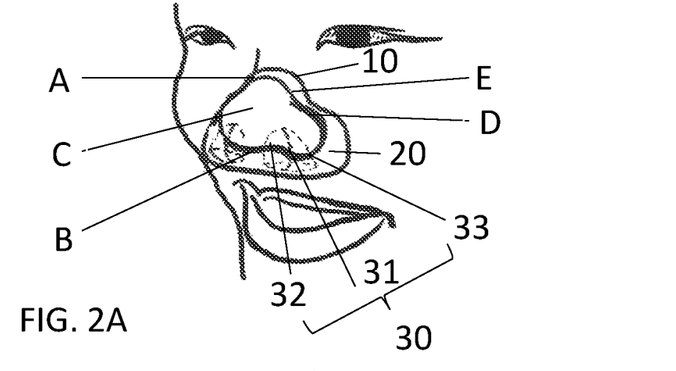
FIG. 2A is a perspective view of a second embodiment of a basic structure for the nose respirator device in accordance with the present invention in which each cavity is divided by a separator into two channels for inhaling and exhaling air, respectively.
Figure 2B:
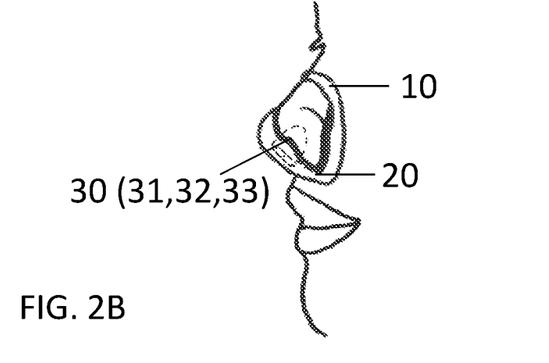
FIG. 2B is a side plan view of the nose respirator in FIG. 2A.
Figure 2C:
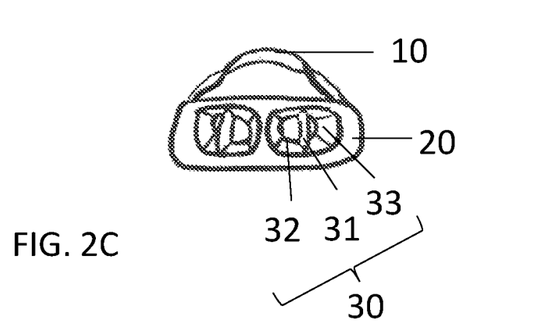
FIG. 2C is a bottom plan view of the nose respirator in FIG. 2A.

With reference to the series of FIGS. 2A to 2C, a second embodiment of a nose respirator device in accordance with the present invention is shown and has the holder (10) and the base (20). The holder in the second embodiment is shaped as a triangle with its top molded for comfortably sitting on and securely hanging from the nasal bridge (A) and its two side arms made to extend down the outside of each of the nose's alae (D) to join with the base (20). The two side arms have a mechanism of pinching inward towards the nasal ridge on the recessed areas (E) above the alae for further securing the holder on the nose. The base sits across the subnasale (B) under the nose tip (C) and has multiple cavities (30), each shaped like a cone in the upper extruded part for being able to be inserted into a nostril. Each cavity is divided by a separator (31) into an inside channel (32) and an outside channel (33). The separator is positioned in such a way so that the inside channel is larger than the outside channel. The separator is shaped in a way to create an aerodynamic situation in which exhaling air normally goes out through the outside channel and inhaling air comes in from the inside channel.

Particularly, the separator is shaped with a contoured curve and positioned inside the cavity in such a way that the exhaled air coming from the top tip of the cavity is reflected into the outside channel and the inhaled air coming in from the inner channel is forced into the inner side of the top tip of the cavity. Each channel can be inserted with its own filter (not shown).

Figure 3A:
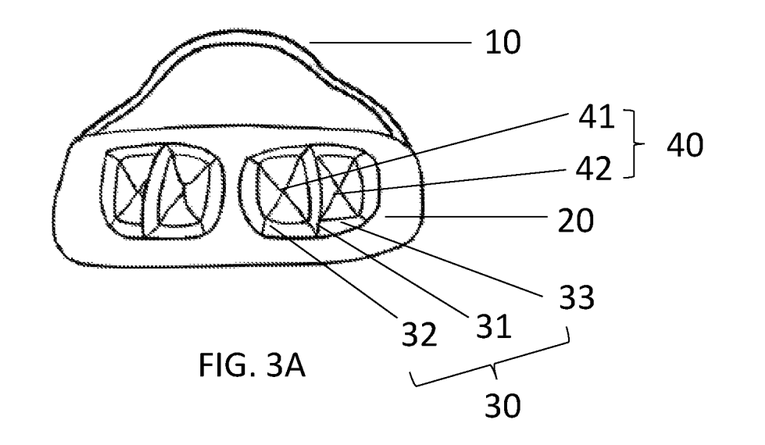
Figure 3B:
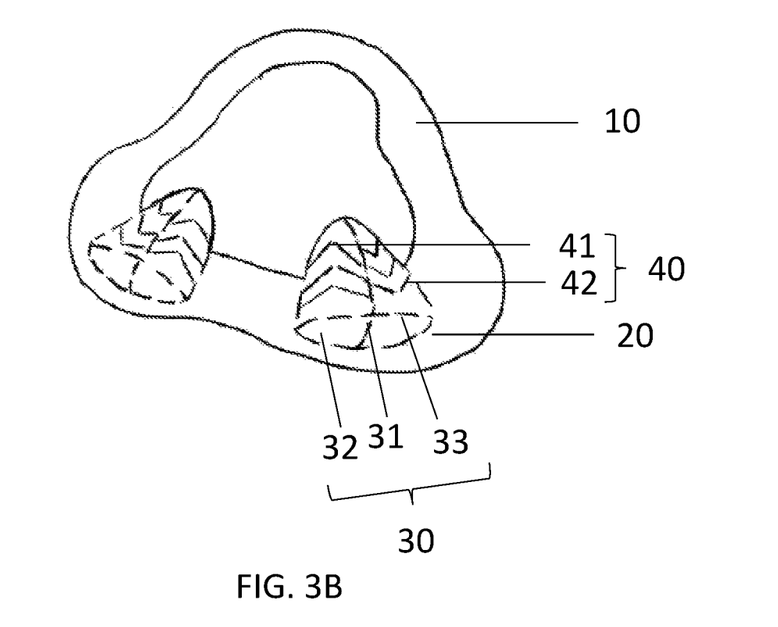

With reference to the series of FIGS. 3A to 3B, a third embodiment of a nose respirator device in accordance with the present invention is shown and has the holder (10) and the base (20). Each cavity (30) inside the base is divided into two channels as described for the second embodiment as shown in FIGS. 2A to 2C. Inside each channel, multiple valves (40) are arranged to provide air flow in one direction. The inner channel valves (41) only allow air to be inhaled. The outer channel valves (42) prevent backflow of exhaled air. More specifically, each inner channel contains valves that open upward when outside air is inhaled into the nose and each outer channel contains valves that open downward when the inside air is exhaled out so that one-direction inhalation and exhalation can be achieved and back flow can be prevented within inner and outer channels, respectively. The valves will be placed at the upper segment of each channel so that they do not interfere with the insertion of a filter. The valves can be made of materials selected from a group consisting of plastic, rubber, fabric, etc.

Figure 4A:
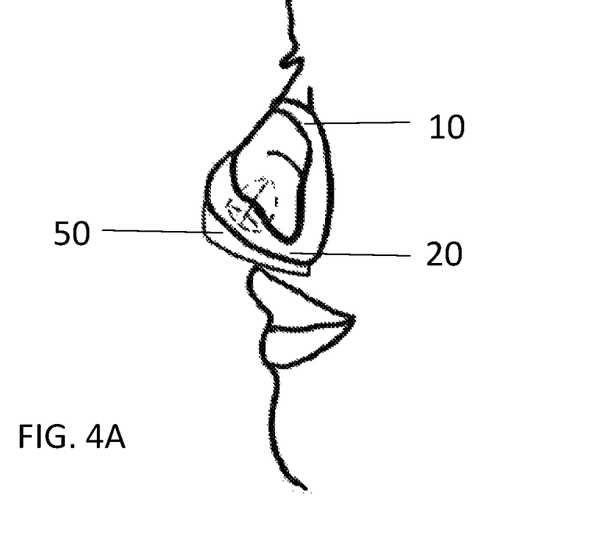
Figure 4B:
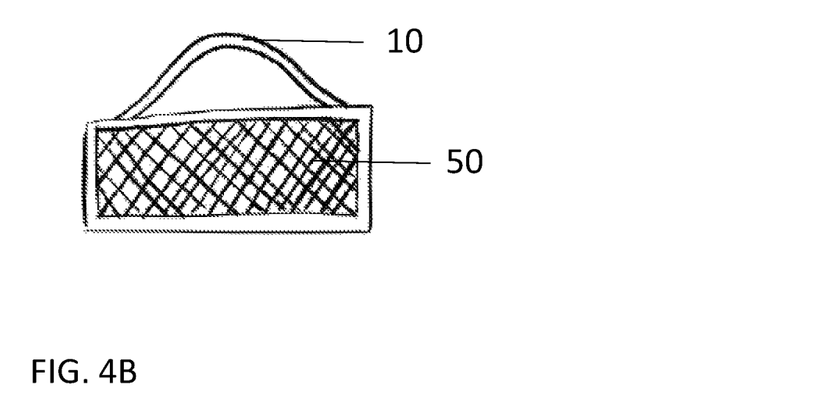

With reference to the series of FIGS. 4A to 4B, a fourth embodiment of a nose respirator device in accordance with the present invention is shown. This embodiment can have the same holder and base as described for the first or the second embodiment but has an additional attachment (50) connected to the bottom of the base (20). This attachment can be an amendment selected from a group of following options: a cassette containing a filtering membrane, which can be either fixed or replaceable, a cassette containing a sorbent soaked with a substance which can provide additional functions, such as sense-stimulating, pathogen disinfection, etc.

Figure 5A:
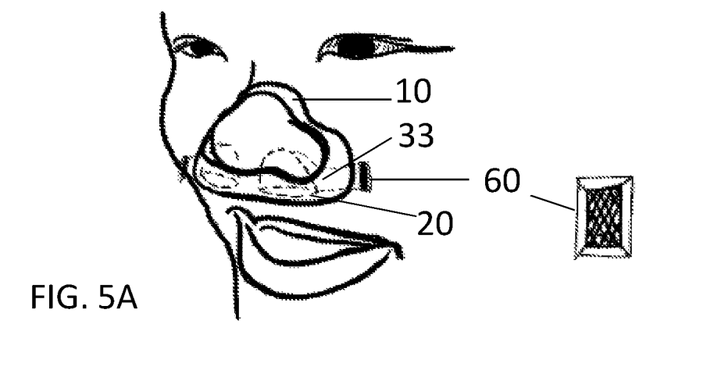
Figure 5B:
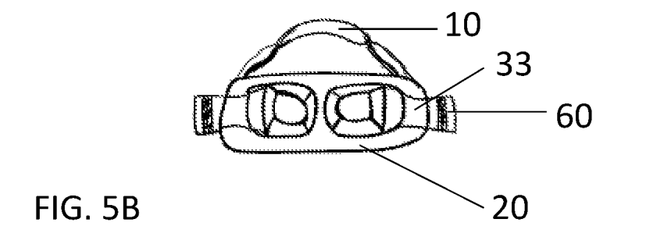

With reference to the series of FIGS. 5A to 5B, a fifth embodiment of a nose respirator device in accordance with the present invention is shown. This embodiment can have the same holder as described for the first or the second embodiment but will have an outside channel (33) in each cavity that opens to the side of the base (20). This side-opening of the outside channel can be fitted with an attachment (60), which is selected from a group consisting of an extended tube containing a filter, an amended plug with a membrane, etc.

Figure 6A:
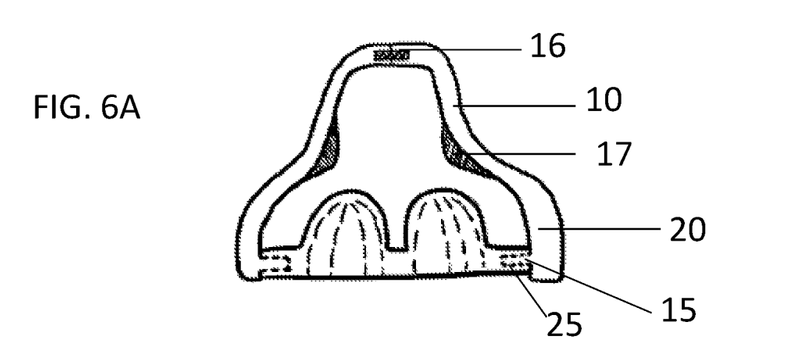
FIG. 6 is a sixth embodiment of a nose respirator device in accordance with the present invention in which the holder and the base are connected with pin-hole couplings and the holder's top is joined with an inner spring.
Figure 6B:
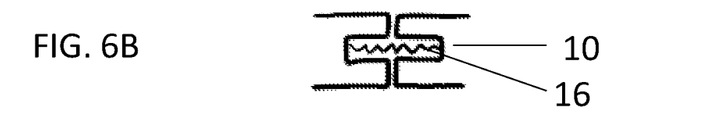
Figure 6C:
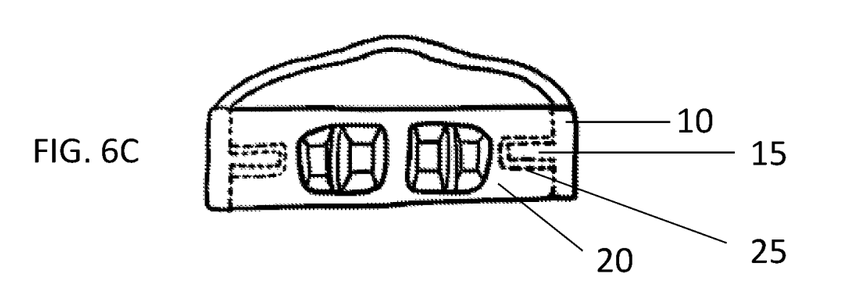

With reference to the series of FIGS. 6A to 6C, a sixth embodiment of a nose respirator device in accordance with the present invention is shown. This embodiment illustrates one way the holder and the base of the invented device can be joined. Specifically, the connection is made by inserting a pin (15) protruded from the holder (10) into a hole (25) in the outer side of the base (20). The holder's top is joined with a spring (16) so that it can open and fit well on the nose when the two arms are pulled outwards. Once worn on the nose, the top of the holder is closed and the extruded soft pads (17) on the two arms of the holder are pushed onto the recessed area above the alae so that the device can be securely worn on the nose.

Figure 7:
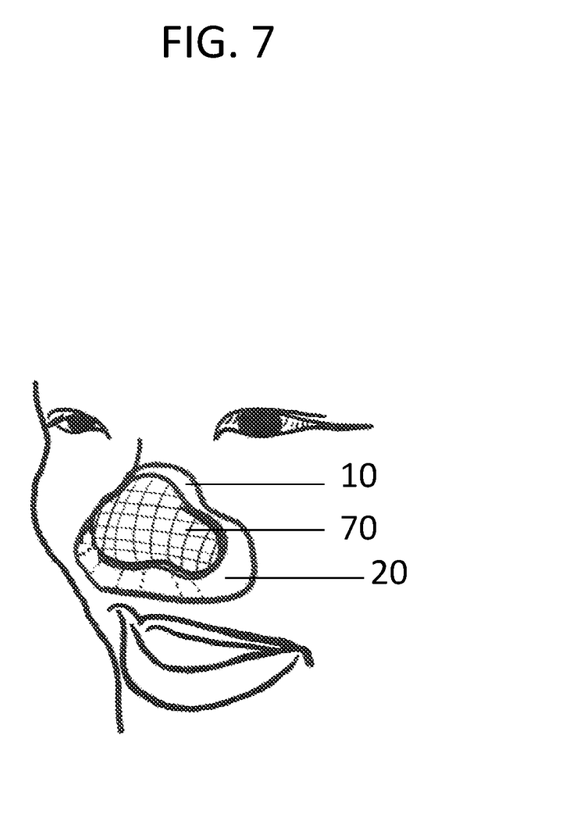
FIG. 7 is a perspective view of a seventh embodiment of a nose respirator device in accordance with the present invention in which the nose holder and the base are all connected by a single sheet (shown with grid) covering the whole lower part of the nose.

With reference to the series of FIG. 7, a seventh embodiment of a nose respirator device in accordance with the present invention is shown in which the open space within the triangle area defined by the holder (10) and the base (20) is covered with a sheet (70) that is joined with the holder and the base and is made of material selected from a group consisting of cloth, plastic, nylon, rubber, etc.

In the first to seventh embodiments, each filter used for the device is selected according to the purpose of the usage of the device. Thus, the types and the specifications of the filters to be used for the device described in this invention will vary.

Providing separate channels for inhalation and exhalation by the present invention offers a variety of advantages for utilizing a device implementing this feature of the invention. First, this will make the filter last longer than other devices that let inhaled and exhaled air pass through the same filter. Secondly, it will make breathing much more comfortable. Thirdly, it will allow the usage of differently configured valves to prevent back flow. Fourthly, it affords multiple ways of adding a variety of attachments to serve different purposes.

To explain the practicality of using separate channels for inhalation and exhalation, following scenarios are presented here for illustrative purposes. For example, pathogens in a patient who uses this kind of nose respirator device will have less opportunity to be bounced back into the respiratory system to cause more damage. A patient using this kind of nose respirator device amended with a disinfection filter attached to the side-opening exhalation channel will release clean air, free of viable pathogens. A patient needing oxygen therapy via nose-tubing can still use this kind of nose respirator device because the inner channels can be used for taking in oxygen and the outer channels for exhaling pathogen-disinfected air. Using separate channels for inhalation and exhalation also make it possible to use different filters for each channel. It also allows filters to be designed and constructed for fitting different aerodynamics of each type of air flow. These advantages offered by the unique designs of the present invention will have great value in fighting the spread of respiratory infectious diseases.

To add stylistic and artistic features to the basic device of the present invention, the holder, the base, and the sheet covering the open areas within the holder and the base can be made out of a variety of materials and transformed into a variety of shapes.

To facilitate the classification of the different types of nose respirator devices created from implementing the present invention and to add identification of the users, each stylistic and artistic feature may be associated with a specific classification of the nose respirator device and identified with its particular usage. For example, health-care providers with high risk of being exposed to a high concentration of infectious viruses may need to wear a high-end, more comprehensive nose respirator device, implementing most of the features provided by the present invention including one or more amendments. A patient suffering a viral infection may need a disinfecting amendment attached to the outside of the exhaling channel so that environmental contamination by the patient can be reduced or, even better, eliminated. Construction workers may need to wear just a nose respirator with filters inside the inhalation channels. Ordinary people doing yard work may need to wear a nose respirator with just valves that are sufficient to prevent coarse particles from getting into their respiratory system. The variety of embodiments of the present invention is not limited by the examples given in this patent specification. Rather, the examples given here mainly serve for illustrational purposes.

Separating the holder from the base in implementing the present invention will allow independent replacement of each according to their actual need. In a practical usage of the nose respirator, the base may need to be replaced more often than the holder, especially when filters contained inside the cavities or channels of the base become dirty. The replacement bases can be stored together as a cassette and packaged in an easy-to-carry way. Furthermore, new replacement filters can be packaged into these transportable sets. Thus, the nose respirators with these embodiments provide great convenience for travel and many opportunities to reduce the material wasting.

Even though numerous characteristics and advantages of the present invention have been set forth in the foregoing description, together with details of the structure and function of the invention, that the disclosure is illustrative only, and changes may be made in details, especially in matters of shape, size, and arrangement of parts within the principles of the invention to the full extent indicated by the broad general meaning of the terms in which the appended claims are expressed is to be understood.

What is claimed is:

1. A nose respirator device having:
    a base sitting across the subnasale underneath the nose tip, the base comprising two open cavities, each open cavity of the two open cavities having an upper opening shaped like a cone with a top tip suitable to be inserted into a nostril;
    a holder, wherein the holder has a top, the top of the holder is configured to sit on the nasal bridge, and wherein the holder has two arms, each arm extending down along one side of the nasal alae; the two arms of the holder are configured to be able to pinch inward towards the nasal bridge on a recessed area above nasal alae for further holding security; and
    a connection mechanism for joining a bottom end of each arm of the holder to each outside side of the base,
    wherein each open cavity of the two open cavities in the base is divided into two channels with a separator, wherein the two channels of each open cavity of the two open cavities in the base are configured as a larger inner channel and a smaller outer channel, respectively; the larger inner channel is proximal to a nasal septum, and the smaller outer channel is distal from the nasal septum; and
    each separator in each open cavity of the two open cavities is shaped with a contoured curve and positioned inside the cavity in such a way that exhaled air coming from the top tip of each cavity of the two open cavities is reflected into the smaller outer channel of each cavity of the two open cavities and inhaled air coming in from the larger inner channel of each cavity of the two open cavities is forced into an inner side of the top tip of each cavity of the two open cavities.

2. The nose respirator device as claimed in claim 1, wherein each inner channel in each cavity of the two open cavities contains valves that open upward with air flowing from bottom of the valves to top of the valves in each cavity of the two cavities and each outer channel in each cavity of the two open cavities contains valves that open downward with air flowing from the top of the valves to the bottom of the valves in each cavity of the two cavities.

3. The nose respirator device as claimed in claim 2, wherein each channel in each cavity of the two open cavities contains a filter below the respective valves, the respective valves being placed in an upper top region of each channel.

4. The nose respirator device as claimed in claim 2, wherein the valves in each channel in each cavity of the two open cavities are arranged in multiple layers along the inside wall of each channel.

5. The nose respirator device as claimed in claim 1, wherein each cavity of the two open cavities contains a filter.

6. The nose respirator device as claimed in claim 1, wherein each channel in each cavity of the two open cavities contains a filter.

7. The nose respirator device as claimed in claim 1, wherein an area inside a triangle defined by the holder and the base is covered with a sheet made from a material selected from the group consisting of cloth, plastic, nylon, and rubber.

\* \* \* \* \*